Figure 1:
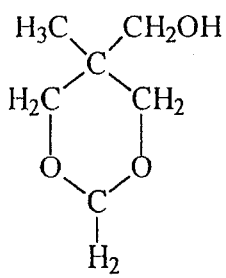
Figure 1:
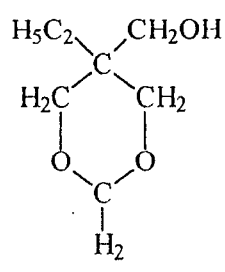
Figure 1:
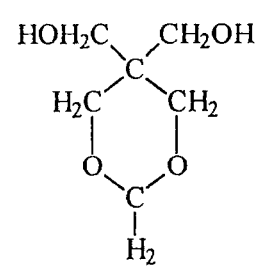
Figure 1:
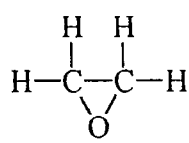
Figure 1:
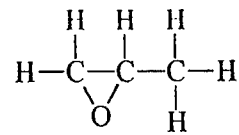
Figure 1:
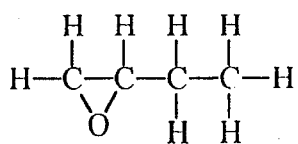
Figure 1:
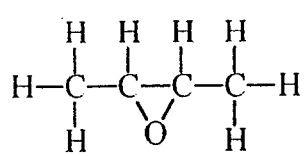
Figure 1:
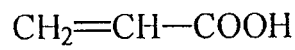
Figure 1:
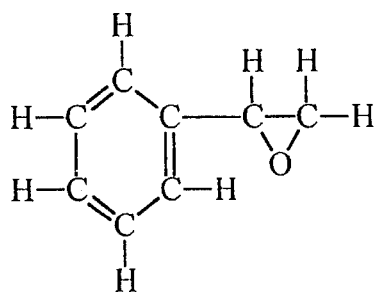
Figure 1:
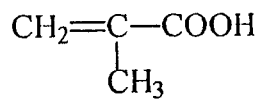

United States Patent [19]

Sörensen

[11] Patent Number: 5,559,201

[45] Date of Patent: Sep. 24, 1996

[54] CYCLOALIPHATIC ACRYLIC MONOMER

[75] Inventor: Kent Sörensen, Perstorp, Sweden

[73] Assignee: Perstorp AB, Perstorp, Sweden

[21] Appl. No.: 492,053

[22] PCT Filed: Apr. 26, 1993

[86] PCT No.: PCT/SE93/00360

§ 371 Date: Jul. 19, 1995

§ 102(e) Date: Jul. 19, 1995

[87] PCT Pub. No.: WO94/17057

PCT Pub. Date: Aug. 4, 1994

[30] Foreign Application Priority Data

Jan. 20, 1993 [SE] Sweden ................................. 9300145

[51] Int. Cl.$^6$ ......................... C08F 224/00; C08F 2/46; C07D 319/06
[52] U.S. Cl. ..................... 526/266; 549/374; 522/184
[58] Field of Search .................... 526/266; 522/184; 549/374

[56] References Cited

U.S. PATENT DOCUMENTS 3,267,084  8/1966  Rankin et al. ................. 526/266
5,004,798  4/1991  Broussard et al. .
5,059,698  10/1991  Schulthess et al. .

FOREIGN PATENT DOCUMENTS 0090174  10/1983  European Pat. Off. .
1900202  8/1970  Germany .

OTHER PUBLICATIONS

Abstract of L.

*Primary Examiner*—Joseph L. Schofer
*Assistant Examiner*—Wu C. Cheng

*Attorney, Agent, or Firm*—Scully, Scott, Murphy & Presser

[57] ABSTRACT

A cycloaliphatic acrylic monomer having the general formula

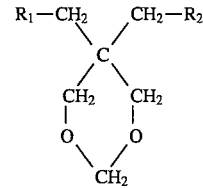

wherein $R_1$ is hydrogen, methyl, hydroxyl, HO—$(R_3)_n$ or

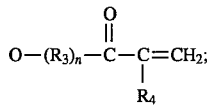

$R_2$ is

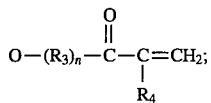

$R_3$ is $C_2H_4O$, $C_3H_6O$, $C_4H_8O$, $C_8H_8O$ or mixtures thereof; $R_4$ is hydrogen or methyl; and n is 1–24. The acrylic monomer is useful as a component in compositions which are radiation curable.

13 Claims, 1 Drawing Sheet

5-Methyl-1,3-dioxane--5-methanol

5-Ethyl-1,3-dioxane--5-methanol 1,3-dioxane--5,5-dimethanol

Ethylene oxide

Propylene oxide 1,2-Butylene oxide 2,3-Butylene oxide

Acrylic acid

Phenylethylene oxide
(Styrene oxide)

Methacrylic acid

CYCLOALIPHATIC ACRYLIC MONOMER

The present invention relates to a cycloaliphatic acrylic monomer based on ethoxylated, propoxylated, butoxylated and/or phenylethoxylated 1,3-dioxane alcohols, which acrylic monomer primarily is intended as a component in radiation curing compositions.

Radiation curing compositions are well-known technologies and used in for instance printing inks, paints and lacquers for furniture and packaging materials as well as for adhesives, but can also comprise application areas such as dental materials. Radiation curing compositions are environmentally suitable and pleasing as they do not contain volatile solvents. They exhibit furthermore a rapid curing and through hardening when exposed to for instance ultraviolet (UV) light or electron-beams (EB). The compositions most often contain one or more oligomers having an unsaturation, normally as acrylate. These oligomers are usually high viscous and are, to obtain applicable viscosities, diluted with various monomers. The monomers are most often acrylic monomers, which monomers are esters of alcohols and acrylic or methacrylic acid. The most commonly used acrylic monomers normally have an acrylate functionality within the range of 1–4.

In radiation curing compositions used acrylic monomers include:

| | |
|---|---|
| Monofunctional: | 2-Ethylhexyl acrylate |
| | 2-(2-ethoxyethoxy)ethyl acrylate |
| | Isobornyl acrylate |
| | Octyldecyl acrylate |
| Difunctional: | Tripropylene glycol diacrylate |
| | 1,6-hexanediol diacrylate |
| | Neopentyl glycol diacrylate |
| | Neopentyl glycol ethoxylate diacrylate |
| Trifunctional: | Pentaerythritol triacrylate |
| | Trimethylolpropane triacrylate |
| | Trimethylolpropane ethoxylate triacrylate |
| | Glycerol propoxylate triacrylate |
| Tetrafunctional: | Pentaerythritol ethoxylate tetraacrylate |
| | Di-trimethylolpropane tetraacrylate |

Some of the above listed acrylic monomers are not included in the list of monomers issued by the Society of British Ink Manufactures Ltd., which list voluntarily exclude monomers that due to for instance a high irritation index or toxicity not are acceptable for use in radiation curing coatings for the printing industry.

High viscous acrylic monomers having an acrylate functionality of 5 and even higher, such as dipentaerythritol pentacrylate, are also used for specific purposes.

Besides the above exemplified acrylic monomers are the cycloaliphatic 5-ethyl-1,3-dioxane-5-methanol monoacrylate and acrylates of allyl alcohols, such as trimethylolpropane allyl ethers, known.

Acrylic monomers are generally highly reactive and as such potentially hazardous being skin and eye irritants and possible sensitizers. The properties in relation to the acrylate functionality can be summarised:
  the lower the acrylate functionality is, the better are the dilution properties and the higher are the skin irritation, toxicity, volatility and odour.
  the higher the acrylate functionality is, the poorer are the dilution properties and the flexibility and the higher are the reactivity, hardness and resistance. Low functional, i.e. mono and difunctional, acrylic monomers must, besides the excellent dilution properties, exhibit low skin irritation and low or no odour to comply with industrial hygienic demands. Above properties must, if the monomers are to be utilised properly, be combined with for instance good reactivity, final hardness and resistance. Presently available mono and difunctional acrylic monomers are most often either skin/eye irritating, highly toxic and/or highly volatile or exhibit poor film forming properties such as poor hardness and/or poor resistance. Thus, the skin irritation value for the above disclosed monomer 5-ethyl-1,3-dioxane-5-methanol monoacrylate has from evaluations performed according to OECD Guideline for Testing of Chemicals no. 404, "Acute Dermal Irritation/Corrosion" of 12 May 1983, been determined to be 2.6/2.8 (erythema/oedema). These values prove, according to "Directive of the Commission 83/467/EEC" of 29 Jul. 1983, as published in "Official Journal of the European Communities" L 257, 1983, that the monomer is to be classified as skin irritant. It can furthermore be noted that neopentyl glycol diacrylate is suspected of being carcinogenic.

The composition and technology of radiation curing systems and acrylic monomers are further disclosed i.a. in "Chemistry & Technology of UV and EB Formulations for Coatings, Inks and Paints"—Volume 2: "Prepolymers and Reactive Diluents for UV and EB Curable Formulations" by N. S. Allen, M. S. Johnson, P. K. T. Oldring and S. Salim. ©1991 Selective Industrial Training Associates Ltd. London, U.K. According to the present invention above disadvantages using mono and difunctional acrylic monomers have been overcome and excellent dilution properties have been combined with low skin irritation, low volatility, low viscosity, good film forming and mechanical properties and good adhesion.

The cycloaliphatic acrylic monomer according to the invention is based on ethoxylated, propoxylated, butoxylated and/or phenylethoxylated 1,3-dioxane alcohols, such as 5-methyl-1,3-dioxane- 5-methanol, 5-ethyl-1,3-dioxane-5-methanol and 1,3-dioxane- 5,5-dimethanol and is characterised in the general formula

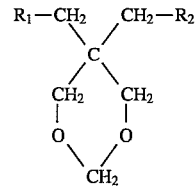

in which formula
$R_1$ is H, $CH_3$, HO, HO—$(R_3)_n$ or

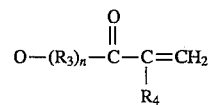

and
$R_2$ is

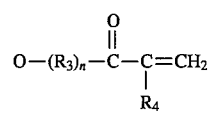

wherein
$R_3$ is $C_2H_4O$, $C_3H_6O$, $C_4H_8O$, $C_8H_8O$ or combinations thereof, $R_4$ is H or $CH_3$ and wherein the mean value $\bar{n}$ for n is 1–24.

It is, besides above disclosed 1,3-dioxane alcohols possible to use derivatives thereof, wherein one or more carbon atoms are alkyl substituted, such as 4-methyl-1,3-dioxane-5,5-di-methanol.

The cycloaliphatic acrylic monomer according to the invention is prepared in at least two steps. Initially the 1,3-dioxane alcohol is ethoxylated, propoxylated, butoxylated and/or phenylethoxylated, which means that ethylene oxide ($R_3=C_2H_4O$), propylene oxide ($R_3=C_3H_6O$), butylene oxide ($R_3=C_4H_8O$) and/or phenylethylene oxide ($R_3=C_8H_8O$) is reacted with the alcohol. A combination such as ethoxylated propoxylate of the 1,3-dioxane alcohol involves two steps. The first step, in such an embodiment, is propoxylation of the alcohol and the second step ethoxylation of the propoxylated alcohol. The resulting product from the ethoxylation, propoxylation, butoxylation and/or phenylethoxylation is finally esterified with acrylic and/or methacrylic acid to obtain the acrylic monomer. Instead of a direct esterification with above acrylic acids can a transesterification using acrylates such as ethyl-acrylate, butylacrylate etc. or corresponding methacryiates, be employed.

Phenylethylene oxide can for specific applications and/or in order to incorporate one or more phenolic rings into the molecule be combined with an ethylene oxide, propylene oxide and/or a butylene oxide. Such a combination can for example suitably be performed by either an intermediate reaction step following the addition step, during which step ethylene oxide, propylene oxide and/or butylene oxide are reacted with the alcohol, and prior to the acrylation step or through an initial reaction step prior to said addition of ethylene oxide, propylene oxide and/or butylene oxide, in which initial step phenylethylene oxide is added to the alcohol. In both cases is phenylethylene oxide added in an amount corresponding to the desired final properties.

The following process is a suitable process for ethoxylation, propoxylation, butoxylation and/or phenylethoxylation of 1,3-dioxane alcohols. The alcohol is charged in a reaction vessel equipped with a stirrer, temperature control and inlet of inert gas. An alkaline compound, such as potassium hydroxide, is thereafter charged as catalyst. The reaction mixture is heated to 100°–160° C. and a pressure of 2000–4000 mm Hg is applied. Ethylene oxide, propylene oxide, butylene oxide and/or phenylethylene oxide (styrene oxide) is then, in an amount resulting in the desired degree of addition, slowly pumped into the reaction vessel. Suitable charging time is about 1 hour followed by a post-reaction during 30 minutes. The obtained product is usually neutralised to pH 6–8 by addition of for instance sodium hydrogenphosphate together with a small amount of water and a filter aid. The water is, after stirring for 1 hour at 100°–150° C., evaporated by vacuum distillation. The product is finally filtered at 100° C. and preferably stabilised by addition of an antioxidant such as butylhydroxytoluene (BHT).

Instead of above described addition, ethylene oxide, propylene oxide, butylene oxide and/or phenylethylene oxide can be replaced by equivalent glycols and/or polyglycols, whereby a conventional etherification is performed.

A suitable process for preparation of an acrylic and/or methacrylic ester of an ethoxylated, a propoxylated, a butoxylated and/or a phenylethoxylated 1,3-dioxane alcohol can be disclosed acid and an azeotropic solvent, such as toluene, are charged into a reaction vessel provided with a stirrer, temperature control, air inlet and a cooler connected to a water-trap. Acrylic or methacrylic acid is charged in excess in relation to desired degree of acrylation and the amount of azeotropic solvent is suitably equal to the subtotal weight of charged raw materials. The reaction mixture is stirred until a clear solution is obtained, a heating to 40°–60° C. may be necessary. Inhibitors such as 2-methyl hydroquinone and nitrobenzene and a catalyst such as sulphonic acid are added and the reaction mixture is heated to reflux using an air sparge. The reflux is maintained until the desired degree of esterification is obtained and formed esterification water is continuously removed azeotropically. When the desired degree of acrylation is obtained, the reaction mixture is cooled to room temperature and neutralised, usually to pH 7–8, with for instance an aqueous solution of sodium hydroxide. The water/salt phase is removed and the product/toluene phase is then repeatedly washed with water. The water phase is after each washing removed. Active carbon and a filter aid are following the washing added to the product/toluene phase, which phase thereafter is filtered. An antioxidant such as 2-methyl hydroquinone, is added to the product/toluene phase and residual toluene is evaporated under vacuum maintaining an air sparge. Acrylation can as alternative to a direct esterification as above, involve a transesterification.

Above described processes are suitable for 1,3-dioxane alcohols and ethoxylated, propoxylated, butoxylated and/or phenylethoxylated 1,3-dioxane alcohols, respectively, but other known processes can of course also be used.

The according to the invention obtained cycloaliphatic acrylic monomer exhibits excellent dilution properties as well as a low skin irritation, a high degree of through hardening, good final hardness, flexibility and resistance.

The cycloaliphatic acrylic monomer according to the invention can favourably be used as a component in radiation curing compositions. The percentage monomer is in such compositions within the range of 0.1–80% by weight, preferably 5–40% by weight. The radiation curing composition can for example be a printing ink, a paint, a lacquer, an adhesive, a dental material or the like. It is, besides radiation curing systems, also possible to use the monomer for the preparation of latex dispersions.

Radiation curing compositions most often comprise one or more oligomers in an amount of 10–80% by weight. Some commonly used oligomers are for instance polyurethane acrylates, polyester acrylates, epoxy acrylates, silicone acrylates and unsaturated polyesters. Radiation curing compositions can furthermore comprise one or more, to the cycloaliphatic monomer according to the invention, additional mono, di and/or multifunctional acrylic monomers in amounts of 0.1–70% by weight. One or more initiators, for example photoinitiators such as benzoephenones and aromatic keto compounds prepared from benzoephenones such as alkylated and halogen-alkylated benzoephenones are also present. Other suitable photoinitiators are for example antraquinones, benzoines and derivatives thereof, acetophenones, acyloxime esters and benzil ketals. The percentage initiator in a radiation curing composition is normally 0.1–10% by weight. Above described compositions can be cured either by means of ultra-violet light or by means of electron-beams (so called UV and EB curing). Curing can also be performed by means of peroxides or other radical forming initiators.

The present invention is further explained in connection to enclosed embodiment examples 1–10 and enclosed FIG. 1, which disclose as follows:

Examples 1 and 2: Ethoxylation of 1,3-dioxane alcohols.

Examples 3 and 4: Acrylation of products according to Examples 1 and 2.

Example 5: Skin irritating properties of the acrylic monomer according to Example 3.

Examples 6 and 7: Preparation of an UV-curing lacquers based on products according to Examples 3 and 4.

Examples 8–11: Evaluations of the UV-curing lacquers according to Example 6 and 7.

FIG. 1: Structural formulas for some selected compounds used as raw materials according to embodiments of the present invention.

The invention is not limited to disclosed embodiments as these can be modified variously within the scope of the invention.

EXAMPLE 1

146 g (1 mole) of 5-ethyl-1,3-dioxane-5-methanol and 3.9 g of powdered potassium hydroxide were weighed into a 1 liter laboratory autoclave. The mixture was heated under stirring and nitrogen purge to 120° C. 132 g (3 moles) of ethylene oxide were during one hour, at a temperature of 120° C. and a pressure of 2000–4000 mm Hg, pumped into the autoclave. A post-reaction was performed during 30 minutes at 120° C. A vacuum of <1 mm Hg was thereafter applied, whereby possibly unreacted ethylene oxide and during the reaction formed low molecular glycols were evaporated. The obtained product was neutralised to pH 6–8 with 3% of sodium hydrogenphosphate together with 1.5% of water and 1.5% of a filter aid (Celite), calculated on charged raw materials. The water was after one hour of stirring at 120° C. during 30 minutes evaporated at this temperature and a vacuum of <1 mm Hg. Finally, the product was filtered at 100° C.

The obtained product consisted of 5-ethyl-1,3-dioxane-5-methanol-triethoxylate having the following characteristics:

Appearance: Clear colourless liquid

Viscosity: 83 mPas at 23° C.

Hydroxyl value: 201 mg KOH/g pH (4% aqueous solution): 5.7

EXAMPLE 2

Example 1 was repeated with the difference that 148 g (1 mole) of 1,3-dioxane-5,5-dimethanol was charged instead of 146 g (1 mole) of 5-ethyl-1,3-dioxane-5-methanol.

The obtained product consisted of 1,3-dioxane-5,5-dimethanol-triethoxylate having the following characteristics:

Appearance: Clear colourless liquid

Viscosity: 520 mPas at 23° C.

Hydroxyl value: 398 mg KOH/g pH (4% aqueous solution ): 6.8

EXAMPLE 3

278 g (1 mole) of the product according to Example 1, 108 g (1.5 mole) of acrylic acid and 400 ml of toluene were charged in a glass flask equipped with a stirrer, air inlet, cooler and water-trap (Dean-Stark). 1600 ppm of 2-methyl hydroquinone and 200 ppm of nitrobenzene as inhibitors and 1.2% of methanesulphonic acid as catalyst were added. The charged components were mixed by stirring until a clear solution was obtained. The reaction mixture was thereafter heated to 120° C. under air sparge. Water formed during the esterification was removed azeotropically. The reflux was maintained until the desired degree of esterification was obtained. The mixture was after 4.5 hours cooled to room temperature and neutralised with a 5% aqueous solution of sodium hydroxide. The water/salt phase was removed and the product/toluene phase was washed three times with water, which after each washing was removed. 5% of active carbon (0.6–1.5 mm Hydraffin BK) and 2% of a filter aid (Celite) was following the washings added to the product/toluene phase, which thereafter was heated to 90° C.

The product/toluene phase was kept at this temperature for 15 minutes, after which time it was cooled to room temperature and filtered. Following the filtration 200 ppm of 2-methyl hydroquinone was added and a vacuum of 20 mm Hg was applied. The residual toluene was evaporated at 20 mm Hg and a temperature of max. 40° C. whilst maintaining an air sparge.

The obtained product consisted of 5-ethyl-1,3-dioxane-5-methanol-triethoxylate monoacrylate having the following characteristics:

Viscosity: 60 mPas at 23° C.

Colour according to Gardner: 3–4

EXAMPLE 4

280 g (1 mole) of the product according to Example 2, 216 g (3 moles) of acrylic acid and 700 ml of toluene were charged in a glass flask equipped with a stirrer, air inlet, cooler and water-trap (Dean-Stark). 1600 ppm of 2-methyl hydroquinone and 200 ppm of nitrobenzene as inhibitors and 1.2% of methanesulphonic acid as catalyst were added. The charged components were mixed by stirring until a clear solution was obtained. The reaction mixture was thereafter heated to 130° C. under air sparge. Water formed during the esterification was removed azeotropically. The reflux was maintained until the desired degree of esterification was obtained. The mixture was after 5 hours cooled to room temperature and neutralised with a 5% aqueous solution of sodium hydroxide. The water/salt phase was removed and the product/toluene phase was washed three times with water, which after each washing was removed. 5% of active carbon (0.6–1.5 mm Hydraffin BK) and 2% of a filter aid (Celite) was following the washings added to the product/toluene phase, which thereafter was heated to 70° C.

The product/toluene phase was kept at this temperature for 15 minutes, after which time it was cooled to room temperature and filtered. Following the filtration 200 ppm of 2-methyl hydroquinone was added and a vacuum of 20 mm Hg was applied. The residual toluene was evaporated at 20 mm Hg and a temperature of max. 40° C. whilst maintaining an air sparge.

The obtained product consisted of 1,3-dioxane-5,5-dimethanol-triethoxylate diacrylate having the following characteristics:

Viscosity: 140 mPas at 23° C.

Colour according to Gardner: 7

EXAMPLE 5

Skin irritation was determined for 5-ethyl-1,3-dioxane-5-methanol-triethoxylate monoacrylate obtained according to Example 2.

The evaluation was carried out in accordance with OECD Guideline for Testing of Chemicals no. 404, "Acute Dermal Irritation/Corrosion", of 12 May 1983. The determination was performed by Scantox A/S, Lille Skensved, Denmark with the following results:

Erythema: 0.4

Oedema: 1.1

According to Directive of the Commission 83/467/EEC, 29 Jul. 1983, published in "Official Journal of the European Communities", L 257, 1983, is 5-ethyl-1,3-dioxane-5-methanol-triethoxylate monoacrylate not to be classified as skin irritating.

EXAMPLE 6

A UV curing lacquer containing the product obtained according to Example 3 was prepared by mixing of below components.

25 parts of acrylic monomer according to Example 3
50 parts of polyester oligomer (Laromer LR 8799, BASF AG, Germany)
25 parts of trimethylolpropane triethoxylate triacrylate
4 parts of UV-initiator (Darocure 1173, Firma E. Merck, Germany);

Obtained lacquer exhibited a viscosity of 335 mPas at 23° C.

EXAMPLE 7

A UV curing lacquer containing the product obtained according to Example 4 was prepared by mixing of below components.

25 parts of acrylic monomer according to Example 4
50 parts of polyester oligomer (Laromer LR 8799, BASF AG, Germany)
25 parts of tripropylene glycol diacrylate
4 parts of UV-initiator (Darocure 1173, Firma E. Merck, Germany)

Obtained lacquer exhibited a viscosity of 286 mPas at 23° C.

EXAMPLE 8

The lacquers obtained according to Examples 6 and 7 were cured by means of a UV-lamp of 80 W/cm and at a belt speed of 20 m/min. The lacquers were coated on glass panels at a filmthickness of 30±5 μm (cured) and were allowed to pass the UV-lamp 1, 2, 4, 8 and 16 times. The samples were after curing tempered for 24 hours at 23°±2° C. and 50±5% relative humidity, whereupon the filmhardness was measured by means of a König pendulum and according to Swedish Standard SS 184186 Edition 4.

The following results were obtained:

|  | Pendulum hardness, König seconds Lacquer according to | |
| --- | --- | --- |
| Number of passages | Example 6 | Example 7 |
| 1 | 35 | 48 |
| 2 | 37 | 57 |
| 4 | 43 | 71 |
| 8 | 52 | 94 |
| 16 | 60 | 115 |

EXAMPLE 9

The lacquers obtained according to Examples 6 and 7 were coated and cured as in Example 8.

The resistance after 16 passages under the UV-lamp was evaluated according to Swedish Standard SS 839118 Edition 2, which fully complies with ISO 4211–1979.

The evaluation scale according to above Standard is 0–5, wherein 5 is best.

The following results were obtained:

|  | Evaluation Lacquer according to | |
| --- | --- | --- |
|  | Example 6 | Example 7 |
| Acetone, 2 minutes | 5 | 5 |
| Ethanol 48%, 16 hours | 5 | 5 |
| Water, 24 hours | 5 | 5 |

EXAMPLE 10

The lacquers obtained according to Examples 6 and 7 were coated on steel panels complying with ISO 1514 at a film-thickness of 30±5 μm (cured) and cured as in Example 8. The scratch resistance as pencil hardness was determined according to ASTM 3363–74 (1989) and the flexibility was determined according to Swedish Standard SS 184177 Edition 3. Both determinations were carried out after 8 passages under the UV-lamp.

The following results were obtained:

|  | Lacquer according to | |
| --- | --- | --- |
|  | Example 6 | Example 7 |
| Scratch resistance | H-2H | HB-F |
| Flexibility | 5.2 mm | 5.3 mm |

EXAMPLE 11

The lacquers obtained according to Examples 6 and 7 were coated and cured as in Example 8.

The degree of hardening through was determined by means of

IR-spectra and as unreacted unsaturation after 1 and 4 passages under the UV-lamp.

The degree of unsaturation in the lacquer prior to curing was normalised to 100.

The degree of hardening through is expressed as 100 minus unreacted unsaturation after curing.

The following results were obtained:

|  | Lacquer according to | |
| --- | --- | --- |
|  | Example 6 | Example 7 |
| Degree of hardening through after 1 passage | 87% | 80% |
| Degree of hardening through after 4 passages | 92% | 83% |

I claim:
1. A cycloaliphatic acrylic monomer comprising compound having the structural formula

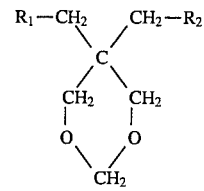

wherein $R_1$ is H, $CH_3$, HO, HO—$(R_3)_n$ or

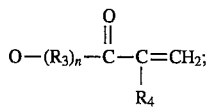

$R_2$ is

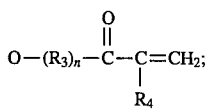

$R_3$ is $C_2H_4O$, $C_3H_6O$, $C_4H_8O$, $C_8H_8O$ or mixtures thereof; $R_4$ is H or $CH_3$; and n is 1–24.

2. An acrylic monomer according to claim 1 wherein $R_3$ is $C_2H_4O$; and n is 2–8.

3. An acrylic monomer according to claim 1 wherein $R_3$ is $C_3H_6O$; and n is 2–6.

4. An acrylic monomer according to claim 1 wherein $(R_3)_n$ is $(C_3H_6O)_m(C_2H_4O)_n$; m is 1; and n is 2–8.

5. A radiation curable composition comprising between 0.1% and 80% by weight, based on the total weight of the composition, of the acrylic monomer of claim 1.

6. A composition according to claim 5 wherein said acrylic monomer comprises between 5% and 40% by weight, based on the total weight of the composition.

7. A composition according to claim 5 wherein said composition is selected from the group consisting of a paint composition, a lacquer composition, a printing ink composition, an adhesive composition and a dental composition.

8. A radiation curable composition comprising between 0.1% and 80% by weight, based on the total weight of the composition, of the acrylic monomer of claim 4.

9. A composition according to claim 8 wherein said acrylic monomer comprises between 5% and 40% by weight, based on the total weight of the composition.

10. A process for preparing a cycloaliphatic acrylic monomer comprising (a) reacting a 1,3-dioxane alcohol with an alkylene oxide selected from the group consisting of ethylene oxide, propylene oxide, butylene oxide, phenylethylene oxide and mixtures thereof, wherein an alkoxylated 1,3-dioxane alcohol having at least one ether bond is formed; and (b) acrylating said alkoxylated 1,3-dioxane alcohol.

11. A process according to claim 10 wherein acrylic acid or methacrylic acid is employed in step (b) to acrylate said alkoxylated 1,3-dioxane alcohol.

12. A process according to claim 10 wherein an acrylate or a methacrylate is employed in step (b) to acrylate said alkoxylated 1,3-dioxane alcohol.

13. A process in accordance with claim 12 wherein said acrylate or said methacrylate is selected from the group consisting of ethyl acrylate, butyl acrylate, ethyl methacrylate and butyl methacrylate.

* * * * *